United States Patent [19]
Canonge et al.

[11] Patent Number: 4,960,927
[45] Date of Patent: Oct. 2, 1990

[54] PROCESS FOR THE CONTINUOUS PREPARATION OF ACETATES

[75] Inventors: Michel Canonge, Martigues; Jean C. Joly, Marseille, both of France

[73] Assignee: BP Chemicals Limited, London, England

[21] Appl. No.: 449,516

[22] Filed: Dec. 5, 1989

Related U.S. Application Data

[63] Continuation of Ser. No. 157,738, Feb. 18, 1988, abandoned.

[30] Foreign Application Priority Data

Feb. 23, 1987 [FR] France .................................. 87 02454

[51] Int. Cl.$^5$ ............................................. C07C 67/02
[52] U.S. Cl. ..................................................... 560/234
[58] Field of Search ................. 560/234; 203/DIG. 6, 203/16, 75, 77, 78

[56] References Cited

U.S. PATENT DOCUMENTS 3,700,726 10/1972 Johnson, Jr. et al. .............. 560/234
4,370,491 1/1983 Bott et al. ........................... 560/234

FOREIGN PATENT DOCUMENTS 970431 9/1964 United Kingdom ................ 560/234

Primary Examiner—Werren B. Lone
Attorney, Agent, or Firm—Brooks Haidt Haffner & Delahunty

[57] ABSTRACT

Figure 1:
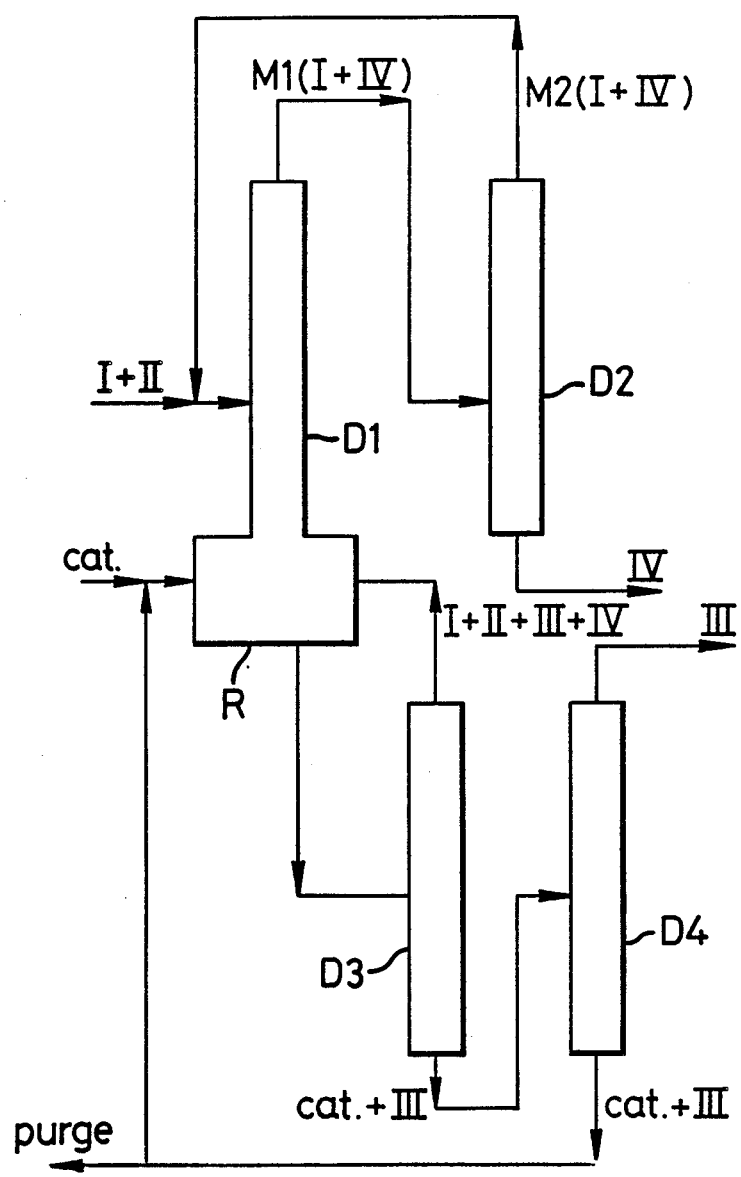

The invention relates to a process for the continuous preparation of acetates by a transesterification reaction in the homogeneous liquid phase in the presence of a catalyst selected from metallic alcoholates. The process comprises more particularly the introduction of the catalyst into a reactor (R) and the introduction of the reagents, comprised of an acetate (I) and an alcohol (II), into a distillation column (D1) surmounting the reactor (R) and operating at a pressure (P1) identical with that in (R). The acetate (III) formed is withdrawn from (R) mixed with the catalyst, which is separated and recycled in (R). An azeotropic mixture (M1), comprising the acetate (I) and the alcohol (IV) formed, emergences at the head of (D1) and feeds a distillation column (D2) at a pressure (P2) lower than (P1), so as to produce at the head of the column an azeotropic mixture (M2) depleted in alcohol (IV), the mixture being recycled in (D1). The process permits the use of relatively humid reagents and alcohols of low reactivity, more particularly secondary alcohols (FIG. 1).

8 Claims, 2 Drawing Sheets

PROCESS FOR THE CONTINUOUS PREPARATION OF ACETATES

This application is a continuation of application Ser. No. 157,738, filed Feb. 18, 1988 now abandoned.

The invention relates to a process for the continuous preparation of acetates by a catalytic transesterification reaction under the homogeneous liquid phase conditions.

It is known to prepare acetates by direct esterification processes consisting in reacting acetic acid or acetic anhydride with an alcohol in the presence of an acid catalyst. However, the industrial use of such processors demands the use of special and expensive equipment because of the corrosive nature of the reagents and catalysts used, more particularly in a reaction medium which generally contains water. These processes are moreover not well adapted to the industrial production of acetates, when alcohols of low reactivity, more particularly alcohols of relatively high molecular weight and secondary alcohols take part in the reaction. It is known that generally the secondary alcohols lead via secondary reactions to the formation of numerous by-products which make it difficult to obtain high purity acetates. Moreover, due to their low reactivity, these alcohols require the use of considerable amounts of catalyst, which themselves encourage the development of the secondary reactions.

It is also known to produce acetates by processes using a catalytic transesterification reaction. In these processes an acetate RA, generally of low molecular weight is brought into contact with an alcohol (R'OH) in the presence of a catalyst chosen from metallic alcoholates, the required acetate (R'A) and a new alcohol (ROH) being obtained by an equilibrium reaction. A process has already been proposed in which the reagents and the catalyst are mixed prior to their introduction into the reactor in which the transesterification reaction takes place. However, having regard to the fact that the catalysts used are highly sensitive to water and quickly become de-activated in a medium containing traces of water, the process must be performed in the complete absence of water. The process must therefore necessarily comprise a preliminary operation to dehydrate the reagents. Nevertheless, to avoid any possible inadequacy in the result of this operation, it is then desirable for the concentration of catalyst in the reaction medium to be relatively high, and unfortunately this may encourage the development of secondary reactions and the formation of undesirable by-products, more particularly when alcohols of low reactivity are used. Such processes are therefore limited to the use of primary alcohols, such as the ethers of monoethylene or diethylene glycol.

It has also been proposed to perform a transesterification reaction in the central zone of a distillation column in the presence of a catalyst selected from alkali metal alcoholates. The catalyst is more particularly introduced into the upper zone of the distillation column, while the reagents are introduced directly into the central zone thereof. Since it therefore passes through the whole distillation zone and more particularly through the reaction zone with a short residence time, the catalyst must be used in a relatively high concentration, and in the case of alcohols of low reactivity, more particularly secondary alcohols, this may unfortunately encourage the development of secondary reactions and the formation of undesirable by-products. The process moreover implies a preliminary reagent dehydration stage, since if the catalyst is used in the presence of inadequately dehydrated reagents it becomes deactivated all the more quickly, since it passes through the whole distillation column. In order to solve these problems, therefore, it has been proposed to perform the transesterification reaction in the heterogeneous phase using the catalyst formed by a solid ion exchange resin which is relatively insensitive to water. However, in that case the reaction temperature cannot exceed 100° C., and this therefore limits the production capacity and the selection of the reagents to be used.

A process has now been found for the continuous preparation of acetates by a catalytic transesterification reaction in the homogeneous liquid phase, which enables the aforementioned difficulties to be obviated. More particularly, the process according to the invention allows the preparation under satisfactory industrial conditions of acetates having a high degree of purity, more particularly when the reagents used are by their chemical nature capable of leading to a relatively slow reaction, or via secondary reactions, to the formation of numerous by-products. The process according to the invention also has the advantage of enabling reagents to be used which are not completely anhydrous, without reducing the catalytic yield of the reaction, expressed by the relation between the quantity of acetate produced and the quantity of catalyst used. This permits the process to be operated without using any preliminary stage of reagent dehydration and enables the moisture content of the products to be controlled, the process being consequently simplified.

The invention therefore relates to a process for the continuous preparation of acetates by a catalytic transesterification reaction using an acetate (I) having the formula $$CH_3COOR_1$$

wherein $R_1$ is an alkyl radical comprising 1–4 carbon atoms, with an alcohol (II) having the formula $$R_2OH$$

wherein $R_2$ is either an alkyl radical comprising at least 4 carbon atoms or a radical having the formula $R_3(OCH_2CHR_4)_n$, wherein $R_3$ is an alkyl radical comprising 1–4 carbon atoms, $R_4$ is a hydrogen atom or a methyl radical and "n" is to be on the normal line level is an integer from 1 to 4, and leading to the formation of an acetate (III) having the formula $$CH_3COOR_2$$

and of an alcohol (IV) having the formula $$R_1OH$$

the reaction being performed in the homogeneous liquid phase in the presence of a catalyst selected from metallic alcoholates, the process being characterised in that:

(a) the catalyst is introduced into a reactor (R) kept at a temperature of from 100° to 200° C. under an absolute pressure (P1) comprised from 0.1 to 1 MPa, (b) the acetate (I) and the alcohol (II) are introduced into a distillation column (D1) connected via its lower portion to the upper portion of the reactor (R) and operating under a pressure substantially identical with that in the reactor (R), (c) at the head of the column (D1) an azeotropic mixture (M1) is separated which is formed by the acetate (I) and the alcohol (IV), the mixture being supplied to a distillation column (D2) operating under an absolute pressure (P2) lower than (P1), (d) the alcohol (IV) is separated at the bottom of the column (D2) and a new azeotropic mixture (M2) is separated at the head of the column which is formed by the acetate (I) and the alcohol (IV) and has an alcohol content (IV) lower than that of the mixture (M1), the new mixture (M2) then being recycled to the column (D1), and (e) a mixture is withdrawn from the reactor (R) which mainly comprises the catalyst and the acetate (III), which is separated and purified, the catalyst being recycled to the reactor (R).

Figure 2:
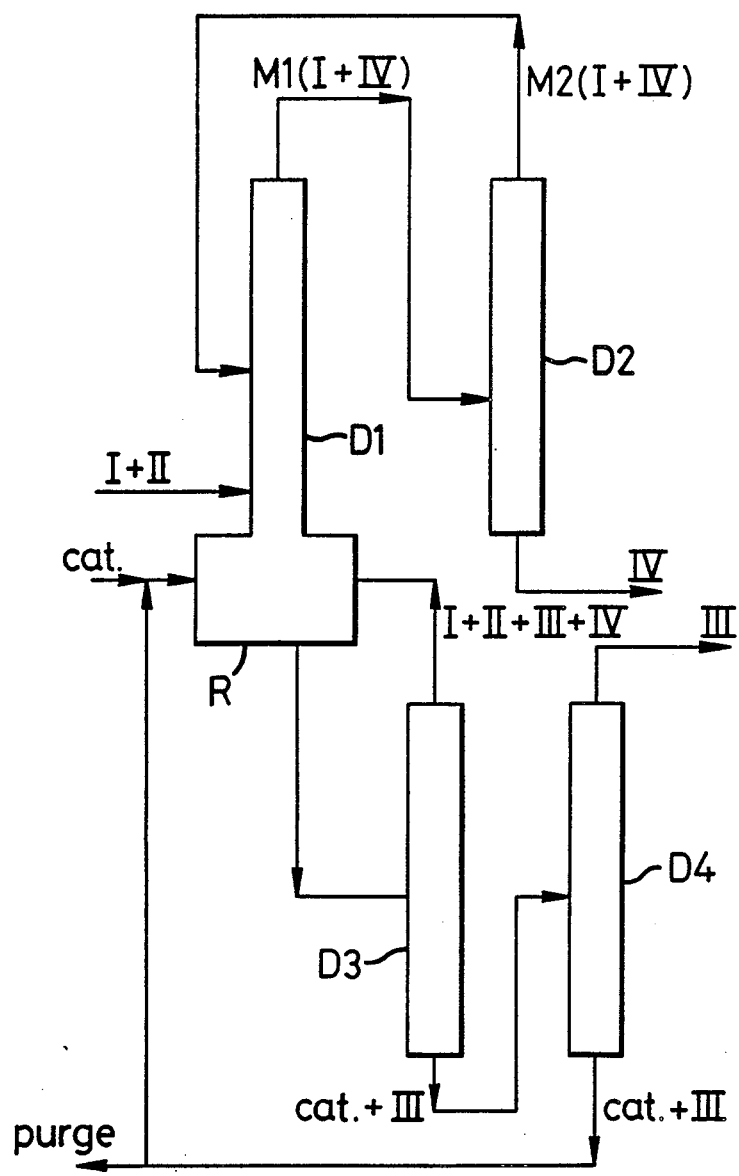

FIGS. 1 and 2 illustrate diagramatically an apparatus used in the process according to the invention, comprising a reactor (R) surmounted by a distillation column (D1) connected to a distillation column (D2), allowing the separation and recycling to the column (D1) of an azeotropic mixture (M2) different from the azeotropic mixture (M1) existing in the column (D1), and also a distillation apparatus comprising distillation columns (D3) and (D4), allowing the separation of the mixture withdrawn from the reactor (R) of the acetate (III) produced by the reaction, the purification thereof and the recycling of the catalyst to the reactor (R).

The acetate (I) used in the process according to the invention has the formula $CH_3COOR_1$, wherein $R_1$ is alkyl radical comprising 1 to 4 carbon atoms. Use is preferably made of methyl acetate, ethyl acetate or n-butyl acetate.

The alcohol (II) can be selected from a large number of organic compounds which have a primary or secondary alcohol function and may more particularly have a relatively high molecular weight. The secondary alcohols can more particularly be used in the transesterification reaction, in the process according to the invention, and lead to the preparation of high purity acetates with the relatively high catalytic yield. The alcohol (II) corresponds to the formula $R_2OH$, wherein $R_2$ can be an alkyl radical comprising in a linear or branched chain at least 4 carbon atoms, preferably 5 to 12 carbon atoms. Use can be made, for example, of 2-ethyl 1-hexanol or 1-octanol. Alcohol (II) can be a glycol ether or polyalkylene glycol ether having the formula $R_2OH$, wherein $R_2$ is a radical having the formula $R_3(OCH_2CHR_4)_n$, wherein $R_3$ is an alkyl radical comprising 1 to 4 carbon atoms, preferably a methyl, ethyl or n-butyl radical, $R_4$ is a hydrogen atom or methyl radical, and n is an integer from 1 to 4 preferably from 1 to 2. In the process according to the invention use can be made of the ethers of ethylene glycol, more particularly of ethers of diethylene glycol. More advantageously use can also be made of the secondary alcohols of relatively high molecular weight, such as the ethers of propylene glycol, more particular methoxy isopropanol, ethoxy isopropanol, the isomers of the methyl ether of dipropylene glycol, and also the isomers of ethyl ether of dipropylene glycol.

The transesterification reaction is performed in the presence of a catalyst selected from metallic alcoholates which are soluble in the liquid reaction medium and more particularly in acetates. The metal present in the catalyst can be selected from the metals belonging to Groups I to IV of the Periodic Table of Elements, more particularly from sodium, potassium, aluminium or titanium. Titanium alcoholates are preferred.

The process according to the invention consists in reacting, in the presence of this catalyst, one mole of acetate (I) with one mole of alcohol (II) in a reactor (R) with a temperature from 100° to 200° C., preferably from 130° to 190° C., at an absolute pressure (PI) of from 0.1 to 1 MPa, preferably comprised between 0.1 and 0.5 MPa. The reactor (R) is connected vis its upper portion to the bottom of the distillation column (D1) wherein an absolute pressure is maintained which is substantially identical to that in the reactor (R). Preferably the reactor (R) is directly surmounted by the column (D1) which is designed to separate at the head an azeotropic mixture (M1) formed by the acetate (I) used and the alcohol (IV) formed. In practice the column (D1) can be a plate column or a packed column and preferably has a theoretical number of plates comprised between approximately 10 and 30.

It is essential in the process according to the invention for the catalyst to be introduced separately from the reagents formed by the acetate (I) and the alcohol (II). More particularly, reagents must not be mixed with the catalyst prior to their introduction into the reaction medium. It is also essential for the reagents formed by the acetate (I) and alcohol (II) to be introduced into the distillation column (D1), while the catalyst is introduced at a relatively large distance and a level lower than that at which the reagents (I) and (II) are introduced into the column (D1). The catalyst is preferably directly introduced into the reactor (R). The acetate (I) and alcohol (II) are introduced into the column (D1) in the liquid state at a level preferably lying in the lower half of the column, and more preferably at a level equal to or higher than the second theoretical plate, counting from the bottom of the column. The acetate (I) and alcohol (II) can be introduced into the column (D1) together—i.e., via a single feed line. In that case they can be mixed prior to their introduction into the column (D1). They can also be introduced separately into the column (D1)—i.e., via two different feed lines which discharge at levels in the column (D1) which are identical or different, but are higher than the level of the catalyst introduction.

It was already known that if reagents such as alcohols of relatively high molecular weight were introduced into a distillation column at a level above the first plates, the functioning of the column might appear less advantageous, more particularly as regards its yield and energy balance. It is therefore unexpected that the preparation of acetates by the process according to the invention is appreciably improved in comparison with the prior art processes, more particularly as regards the catalytic yield of the reaction.

It was also previously known that if water is present in the reaction medium, not only was the catalyst quickly deactivated, but the water was capable of forming azeotropes with the alcohols and the acetates, thus rendering the separation and purification of the products more complex. The process according to the invention can be performed using reagents having a possible water content from about 100 ppm and up to at least 1000 ppm and even to 20,000 ppm with relatively small reduction in the catalytic yield of the reaction, acetate (III) being readily obtained with a high degree of purity and a low residual acidity.

A mixture is withdrawn from the reactor (R) which mainly comprises the acetate (III) and small quantities of the alcohols (II) and (IV), the acetate (I) and the catalyst. Using normal distillation techniques, from the mixture are separated from the acetate (III), which can then be purified by a simple distillation, and the catalyst, which is recycled in the reactor (R). First, according to one of the numerous possible variants, the mixture leaving the reactor (R) can supply a distillation column (D3) operating under conditions such that at its head a mixture is withdrawn which comprises all the products present in the production medium except the catalyst, such mixture being directly recycled to the reactor (R), a mixture mainly formed by the acetate (III) and the catalyst being separated at the bottom of the column. This latter mixture can be fed to a distillation column (D4) operating under conditions such that the acetate (III) is withdrawn at the head of the column with a degree of purity higher than 99.5%, a mixture mainly containing the catalyst and the acetate (III) being separated at the bottom of the column. The distillation columns (D3) and (D4), can be plate columns or packed columns having a number of theoretical plates preferably in the range 3 to 30. The two columns preferably operate at a pressure lower than atmospheric pressure, more particularly when the acetate (III) has a relatively high molecular weight. The mixture emerging at the bottom of the column (D4) is mainly recycled to the reactor (R) at a point identical to or different from that where fresh catalyst is introduced. A small proportion of this mixture, more particularly containing deactivated catalyst, is discharged via a drain situated on the catalyst recycling line. The result is that to maintain a constant catalyst concentration in the reaction medium, a further quantity of fresh catalyst, equivalent to the quantity of catalyst drained off, must be added to the reactor (R). An important advantage of this process is that the majority of catalyst participating in the reaction originates from catalyst recycling, the additional quantity of fresh make-up catalyst being relatively low, as a rule not exceeding 3% by weight and preferably not exceeding 1.5% by weight of the total quantity of catalyst participating in the reaction. The amount of catalyst consumed can be less than 0.1% by weight and preferably less than 0.05% by weight of the quantity of acetate (III) produced.

An azeotropic mixture (M1) formed by the acetate (I) used and the alcohol (IV) formed is separated at the head of the distillation column (D1). The mixture (M1) is fed to a distillation column (D2) operating at an absolute pressure (P2) which must be appreciably lower than the absolute pressure in the reactor (R) and the column (D1) so as to facilitate the separation of the alcohol (IV) from the azeotropic mixture (M1). The absolute pressure (P2) is generally lower than atmospheric pressure and more particularly from 0.1 to 0.06 Mpa. The column (D2) is designed to separate the alcohol (IV) at the bottom and a new azeotropic mixture (M2) at the head which is formed by the acetate (I) and the alcohol (IV) having a content of alcohol (IV) lower than that of the mixture (M1). In practice the column (D2) can be a plate column or a packed column preferably having a number of theoretical plates in the range 10 to 30. The new azeotropic mixture (M2) is recycled directly in the column (D1) at a level identical with or different from that where the reagents (I) and (II) are introduced. It is preferably introduced at a level as indicated in FIG. 1, or higher than the level at which the reagents (I) and (II) are introduced, more particularly at a level lying in the lower half of the column (D1), as shown in FIG. 2.

The process according to the invention is particularly advantageous for the continuous preparation of acetates having a high degree of purity from alcohols of relatively high molecular weight, alcohols of low activity and more particularly secondary alcohols, such as ethers of propylene glycol. It more particularly enables the formation of undesirable by-products to be prevented when secondary alcohols participate in the reaction. Another important advantage resulting from the invention consists in the possibility of using directly in the reaction reagents which are not completely anhydrous, without the catalytic yield of the reaction being substantially reduced and without the separation and purification of the acetate (III) being made more complex. For example, a large variety of acetates (I) and alcohols (II) produced industrially and possibly containing from about 100 ppm up to about 1000 ppm and even to about 20,000 ppm of water can be used directly in the process according to the invention, thus eliminating the need for any preliminary stage for dehydrating such reagents. Relatively small amounts of fresh catalyst are required to be added to the process according to the invention.

The following examples illustrate the invention.

EXAMPLE 1

Methoxy isopropyl acetate (III) was continuously prepared in an installation shown diagramatically in FIG. 1 and comprising a reactor (R) having a volume of 25 m$^3$, surmounted by a distillation column (D1) having a height of 18 m and a diameter of 1.7 m and comprising 30 plates with bubble caps, corresponding to 18 theoretical plates.

At the level of the 11th plate, counting from the bottom of the column (D1), an equimolar mixture of ethyl acetate (I) and methoxy isopropanol (II) having a water content of 700 ppm was introduced to the column at a regular flow rate of 5380 kg/h. At the same time titanium tetraethylate was introduced as a catalyst at a flow rate of 3 kg/h directly into the liquid reaction medium present in the reactor (R), maintained at a temperature of 144° C. and an absolute pressure (P1) of 0.33 MPa.

To maintain a constant volume of liquid of 20 m$^3$ in the reactor (R), a mixture was withdrawn from its bottom at a flow rate of 8268 kg/h which comprised mainly methoxy isopropyl acetate (III) and small quantities of ethyl acetate (I), methoxy isopropanol (II), ethanol (IV) and the catalyst. At the level of the sixth theoretical plate counting from the bottom, the mixture was supplied to a distillation column (D3) having a height of 11 m and a diameter of 1.6 m, the column being a packed column corresponding to 18 theoretical plates and operating at an absolute pressure of 0.04 MPa, with bottom and head temperatures of 118° C. and 82° C. respectively. At the head of the column a mixture was withdrawn at a flow rate of 4108 kg/h which contained all the products present in (R), except the catalyst. At the bottom of the column (D3) a mixture of methoxy isopropyl acetate (III) and catalyst was withdrawn at a flow rate of 4160 kg/h and fed, at the level of the first theoretical plate counting from the bottom, to a distillation column (D4) having a height of 4 m and a diameter of 1 m, the column being a packed column corresponding to 4 theoretical plates and operating at an absolute pressure of 0.018 MPa, with bottom and head temperatures of 120° C. and 95° C. respectively. At the head of the column (D4) methoxy isopropyl acetate (III) was withdrawn at a flow rate of 4000 kg/h which had a degree of purity higher than 99.5% and a residual acidity lower than 50 ppm, expressed in acetic acid. At the bottom of the column a mixture containing the catalyst and methoxy isopropyl acetate (III) in a ratio by weight of 75/25 was withdrawn at a flow rate of 660 kg/h. A proportion of the mixture was drained off at a flow rate of about 4 kg/h. The rest of the mixture was recycled and introduced at a flow rate of 656 kg/h directly to the reactor (R) at the same point of introduction as that of the fresh catalyst.

The distillation column (D1) operated at an absolute pressure (P1) of 0.33 MPa, with bottom and head temperatures of 144° C. and 107° C. respectively. At the head of the column an azeotropic mixture (M1) formed by ethyl acetate (I) and ethanol (IV) at a ratio by weight of 58/42 was withdrawn at a flow rate of 5827 kg/h.

The mixture (M1) was fed, at the level of the ninth plate counting from the bottom, to a distillation column (D2) having a height of 18 m and a diameter of 1.7 m, comprising 30 plates with bubble caps corresponding to 18 theoretical plates and operating at an absolute pressure (P2) of 0.03 MPa, with bottom and head temperatures of 52° C. and 40° C. respectively. At the head of the column a fresh azeotropic mixture (M2) formed by ethyl acetate (I) and ethanol (IV) in a ratio by weight of 76/24 was withdrawn at a flow rate of 4447 kg/h. The fresh mixture (M2) was recycled and introduced into the column (D1) at the same point of introduction as that of the reagents (I) and (II)—i.e., at the level of the eleventh plate, counting from the bottom of the column. Ethanol (IV) was withdrawn from the bottom of the column (D2) at a flow rate of 1380 kg/gh.

EXAMPLE 2

Ethoxy isopropyl acetate (III) was continuously prepared in an installation shown diagramatically in FIG. 2 and comprising a reactor (R) having a volume of 20 m$^3$, surmounted by a distillation column (D1) having a height of 18 m and a diameter of 1.7 m and comprising 30 plates with bubble caps, corresponding to 18 theoretical plates.

At the level of the fourth plate, counting from the bottom of the column (D1), an equi-molar mixture of ethyl acetate (I) and ethoxy isopropanol (II) having a water content of 600 ppm was introduced into the column at a regular flow rate of 5248 kg/h. At the same time titanium tetraethylate was introduced as a catalyst at a flow rate of 3 kg/h directly into the liquid reaction medium present in the reactor (R), maintained at a temperature of 149° C. and an absolute pressure (P1) of 0.33 MPa.

To maintain a constant volume of liquid of 20 m$^3$ in the reactor (R), a mixture mainly comprising ethoxy isopropyl acetate (III) and small quantities of ethyl acetate (I), ethoxy isopropanol (II), ethanol (IV) and the catalyst was withdrawn from its bottom at a flow rate of 8251 k/h. At the level of the sixth theoretical plate, counting from the bottom, the mixture was supplied to a distillation column (D3) having a height of 11 m and a diameter of 1.6 m, the column being a packed column corresponding to 18 theoretical plates and operating at an absolute pressure of 0.033 MPa and bottom and head temperatures of 124° C. and 89° C. respectively. At the head of the column a mixture containing all the products present in the reactor (R) except the catalyst was withdrawn at a flow rate of 4090 kg/h. At the bottom of the column (D3) a mixture of ethoxy isopropyl acetate (III) and catalyst was withdrawn at a flow rate of 4160 kg/h and supplied, at the level of the first theoretical plate counting from the bottom, to a distillation column (D4) having a height of 4 m and a diameter of 1 m, the column being a packed column corresponding to 4 theoretical plates and operating at an absolute pressure of 0.014 MPa and bottom and head temperatures of 125° C. and 100° C. respectively. At the head of the column (D4), ethoxy isopropyl acetate (III) was withdrawn at a flow rate of 4000 kg/h which had a degree of purity higher than 99.5% and a residual acidity lower than 50 ppm, expressed in acetic acid. At the bottom of the column a mixture containing the catalyst and ethoxy isopropyl acetate (III) in a proportion by weight of 80/20 was withdrawn at a flow rate of 860 kg/h. A proportion of the mixture was drained off at a flow rate of about 4 kg/h. The remainder of the mixture was recycled and introduced at a flow rate of 856 kg/h directly into the reactor (R) at the same level of introduction as that of the fresh catalyst.

The distillation column (D1) operated at an absolute pressure (P1) of 0.33 MPa, with bottom and head temperatures of 149° C. and 107° C. respectively. At the head of the column an azeotropic mixture (M1) formed by ethyl acetate (I) and ethanol (IV) in a proportion by weight by 58/42 was withdrawn at a flow rate of 5268 kg/h.

The mixture (M1) was supplied, at the level of the ninth plate counting from the bottom, to a distillation column (D2) having a height of 18 m and a diameter of 1.7 m, comprising 30 plates with bubble caps corresponding to 18 theoretical plates, and operating at an absolute pressure (P2) of 0.03 MPa, with bottom and head temperatures of 52° C. and 40° C. respectively. At the head of the column a fresh azeotropic mixture (M2) formed by ethyl acetate (I) and ethanol (IV) in a proportion by weight of 76/24 was withdrawn at a flow rate of 4020 kg/h. The fresh mixture (M2) was recycled and introduced into the column (D1) at the level of the eleventh plate counting from the bottom of the column. Ethanol (IV) was withdrawn from the bottom of the column (D2) at a flow rate of 1248 kg/h.

EXAMPLE 3

The acetate of the butyl ether of diethylene glycol (III) was continuously prepared in an installation shown diagramatically in FIG. 1 and comprising a reactor (R) having a volume of 25 m$^3$, surmounted by a distillation column (D1) having a height of 18 m and a diameter of 1.7 m and comprising 30 plates with bubble caps corresponding to 18 theoretical plates.

At the level of the eleventh plate counting from the bottom of the column (D1), an equimolar mixture of ethyl acetate (I) and butyl ether of diethylene glycol (II) having a water content of 600 ppm was introduced into the column at a regular flow rate of 3670 kg/h. At the same time titanium tetraethylate was introduced as a catalyst at a flow rate of 0.12 kg/h directly into the liquid reaction medium present in the reactor (R), maintained at a temperature of 185° C. and an absolute pressure (P1) of 0.2 MPa.

To maintain a constant volume of liquid of 6 m$^3$ in the reactor (R) a mixture comprising mainly the acetate of the butyl ether of diethylene glycol (III) and small quantities of ethyl acetate (I), the butyl ether of diethylene glycol (II), ethanol (IV) and the catalyst was withdrawn from the bottom of the reactor at a flow rate of 3893 kg/h. The mixture was supplied, at the level of the sixth theoretical plate counting from the bottom, to a distillation column (D3) having a height of 11 m and a diameter of 1.6 m, the column being a packed column corresponding to 18 theoretical plates and operating at an absolute pressure of 0.016 MPa, with bottom and head temperatures of 185° C. and 154° C. respectively. At the head of the column a mixture containing all the products present in the reactor (R) except the catalyst was withdrawn at a flow rate of 863 kg/h. At the bottom of the column (D3) a mixture of the acetate of the butyl ether of diethylene glycol (III) and catalyst was withdrawn at a flow rate of 3030 kg/h and supplied, at the level of the first theoretical plate counting from the bottom, to a distillation column (D4) having a height of 4 m and a diameter of 1 m, the column being a packed column corresponding to 4 theoretical plates and operating at an absolute pressure of 0.007 MPa, with bottom and head temperatures of 175° C. and 156° C. respectively. At the head of the column (D4) the acetate of the butyl ether of diethylene glycol (III) having a degree of purity higher than 99.5% and a residual acidity lower than 50 ppm, expressed in acetic acid, was withdrawn at a flow rate of 3000 kg/h. At the bottom of the column a mixture containing the catalyst and acetate of the butyl ether of diethylene glycol (III) in a proportion by weight of 40/60 was withdrawn at flow rate of 50 kg/h. A proportion of the mixture was drained off at a flow rate of about 0.3 kg/h. The remainder of the mixture was recycled and introduced at a flow rate of 49.7 kg/h directly in the reactor (R) at the same point of introduction as that of the fresh catalyst.

The distillation column (D1) operated at a pressure (P1) of 0.2 MPa, with bottom and head temperatures of 185° C. and 90° C. respectively. At the head of the column an azeotropic mixture (M1) formed by ethyl acetate.(I) and ethanol (IV) in a proportion by weight of 58/42 was withdrawn at a flow rate of 4172 kg/h.

The mixture (M1) was supplied, at the level of the ninth plate counting from the bottom to a distillation column (D2) having a height of 18 m and a diameter of 1.7 m, comprising 30 plates with bubble caps corresponding to 18 theoretical plates, and operating at an absolute pressure (P2) of 0.03 MPa, with bottom and head temperatures of 52° C. and 40° C. respectively. At the head of the column a fresh azeotropic mixture (M2) formed by ethyl acetate (I) and ethanol (IV) in a ratio by weight of 76/24 was withdrawn at a flow rate of 3502 kg/h. The fresh mixture (M2) was recycled and introduced into the column (D1) at the same point of introduction as that of the reagents (I) and (II)—i.e., at the level of the eleventh plate counting from the bottom of the column. Ethanol (IV) was withdrawn from the bottom of the column (D2) at a flow rate of 670 kg/h.

EXAMPLE 4

Methoxyisopropyl acetate (III) was continuously prepared in an installation shown diagramatically in FIG. 1 and comprising a reactor (R) having a volume of 25 m$^3$, surmounted by a distillation column (D1) having a height of 18 m and a diameter of 1.7 m and comprising 30 plates with bubble caps corresponding to 18 theoretical plates.

At the level of the eleventh plate counting from the bottom of the column (D1), an equimolar mixture of methoxyisopropanol (II) and an azeotrope of methanol/methyl acetate (I) containing 15% weight of methanol having a water content of 15,000 ppm was introduced into the column at a regular flow rate of 5352 kg/h. At the same time titanium tetraethylate was introduced as a catalyst at a flow rate of 3 kg/h directly into the liquid reaction medium present in the reactor (R), maintained at a temperature of 155° C. and an absolute pressure (P1) of 0.53 of MPa.

To maintain a constant volume of liquid of 20 m$^3$ in the reactor (R) a mixture comprising mainly the methoxyisopropyl acetate (III) and small quantities of methylacetate (I), methoxyisopropanol (II), methanol (IV) and the catalyst was withdrawn from the bottom of the reactor at a flow rate of 7738 kg/h. The mixture was supplied, at the level of the sixth theoretical plate counting from the bottom, to a distillation column (D3) having a height of 11 m and a diameter of 1.6 m, the column being a packed column corresponding to 18 theoretical plates and operating at an absolute pressure of 0.053 MPa, with bottom and head temperatures of 126° C. and 90° C. respectively. At the head of the column a mixture containing all the products present in the reactor (R) except the catalyst was withdrawn at a flow rate of 3497 kg/h. At the bottom of the column (D3) a mixture of the methoxyisopropylacetate (III) and catalyst was withdrawn at a flow rate of 4241 kg/h and supplied, at the level of the first theoretical plate counting from the bottom, to a distillation column (D4) having a height of 4 m and a diameter of 1 m, the column being a packed column corresponding to 4 theoretical plates and operating at an absolute pressure of 0.016 MPa, with bottom and head temperatures of 120° C. and 90° C. respectively. At the head of the column (D4) methoxyisopropylacetate (III) having a degree of purity higher than 99.5% and a residual acidity lower than 50 ppm, expressed in acetic acid, was withdrawn at a flow rate of 4000 kg/h. At the bottom of the column a mixture containing the catalyst and methoxyisopropylacetate (III) in a proportion by weight of 60/40 was withdrawn at flow rate of 241 kg/h. A proportion of the mixture was drained off at a flow rate of about 3 kg/h. The remainder of the mixture was recycled and introduced at a flow rate of 238 kg/h directly in the reactor (R) at the same point of introduction as that of the fresh catalyst.

The distillation column (D1) operated at a pressure (P1) of 0.53 MPa, with bottom and head temperatures of 155° C. and 107° C. respectively. At the head of the column an azeotropic mixture (M1) formed by methyl acetate (I) and methanol (IV) in a proportion by weight of 71/29 g was withdrawn at a flow rate of 8538 kg/h.

The mixture (M1) was supplied, at the level of the ninth plate counting from the bottom to a distillation column (D2) having a height of 18 m and a diameter of 1.7 m, comprising 30 plates with bubble caps corresponding to 18 theoretical plates, and operating at an absolute pressure (P2) of 0.053 MPa, with bottom and head temperatures of 52° C. and 38° C. respectively. At the head of the column a fresh azeotropic mixture (M2) formed by methyl acetate (I) and methanol (IV) in a ratio by weight of 84/16 with withdrawn at a flow rate of 7186 kg/h. The fresh mixture (M2) was recycled and introduced into the column (D1) at the same point of introduction as that of the reagents (I) and (II)—i.e., at the level of the eleventh plate counting from the bottom of the column. Methanol (IV) was withdrawn from the bottom of the column (D2) at a flow rate of 1352 kg/h.

We claim:

1. A process for the continuous preparation of acetates by a catalytic transesterification reaction using an acetate (I) having the formula $$CH_3COOR_1$$

wherein $R_1$ is an alkyl radical comprising 1-4 carbon atoms, with an alcohol (II) having the formula $$R_2OH$$

wherein $R_2$ is either an alkyl radical comprising at least 4 carbon atoms, or a radical having the formula $R_3(OCH_2CHR_4)_n$, Wherein $R_3$ is an alkyl radical comprising 1-4 carbon atoms, $R_4$ is a hydrogen atom or a methyl radical and n is an integer from 1 to 4, and leading to the formation of an acetate (III) having the formula $$CH_3COOR_2$$

and of an alcohol (IV) having the formula $$R_1OH$$

the reaction being performed in the homogeneous liquid phase in the presence of a catalyst selected from metallic alcoholates, the process being characterised in that:
 (a) the catalyst is introduced into a reactor (R) kept at a temperature of from 100° to 200° C. under an absolute pressure (P1) from 0.1 to 1 MPa,
 (b) the acetate (I) and the alcohol (II) are introduced into a distillation column (D1) connected via its lower portion to the upper portion of the reactor (R) and operating under a pressure substantially identical with that in the reactor (R),
 (c) at the head of the column (D1) an azeotropic mixture (M1) is separated which is formed by the acetate (I) and the alcohol (IV), the mixture being supplied to a distillation column (D2) operating under an absolute pressure (P2) lower than (P1),
 (d) the alcohol (IV) is separated at the bottom of the column (D2) and a new azeotropic mixture (M2) is separated at the head of the column which is formed by the acetate (I) and the alcohol (IV) and has an alcohol (IV) content lower than that of the mixture (M1), the new mixture (M2) then being recycled to the column (D1), and
 (e) a mixture is withdrawn from the reactor (R) which mainly comprises the catalyst and the acetate (III), which is separated and purified, the catalyst being recycled to the reactor (R).

2. A process according to claim 1 characterised in that the acetate (I) is selected from the group consisting of methyl acetate, ethyl acetate and n-butyl acetate.

3. A process according to claim 1 characterised in that the alcohol (II) is a secondary alcohol.

4. A process according to claim 1 characterised in that the alcohol (II) is selected from the group consisting of methoxy isopropanol, ethoxy isopropanol, the isomers of the methyl ether of dipropylene glycol and the isomers of the ethyl ether of dipropylene glycol.

5. A process according to claim 1 characterised in that the catalyst is a metallic alcoholate comprising a metal selected from the metals belonging to groups (I) to (IV) of the Periodic Table of Elements.

6. A process according to claim 1 characterised in that the catalyst is a titanium alcoholate.

7. A process according to claim 1 characterised in that the acetate (I) and the alcohol (II) are directly introduced, separately or mixed together, into the column (D1) at a level situated in the lower half of the column.

8. A process according to claim 1 characterised in that the azeotropic mixture (M2) is recycled directly into the column (D1) at a level identical with or higher than that where the acetate (I) and the alcohol (II) are introduced.

* * * * *

UNITED STATES PATENT AND TRADEMARK OFFICE
CERTIFICATE OF CORRECTION

PATENT NO. : 4,960,927

DATED : October 2, 1990

INVENTOR(S) : Michel Canonge et al

It is certified that error appears in the above-identified patent and that said Letters Patent is hereby corrected as shown below:

Column 4, l. 11, change "vis" to --via--

Column 7, l. 61, change "k/h" to --kg/h--.

Claim 1, l. 14, correct the spelling of --wherein--.

Signed and Sealed this

Thirty-first Day of March, 1992

Attest:

HARRY F. MANBECK, JR.

*Attesting Officer*  *Commissioner of Patents and Trademarks*